United States Patent [19]

Seifert et al.

[11] Patent Number: 5,776,118
[45] Date of Patent: Jul. 7, 1998

[54] MEDICAL AND BIOLOGICAL FLUID COLLECTION AND DISPOSAL SYSTEM

[75] Inventors: Raymond C. Seifert, Chardon; John R. Bradbury, Strongsville, both of Ohio

[73] Assignee: Steris Corporation, Mentor, Ohio

[21] Appl. No.: 571,533

[22] Filed: Dec. 13, 1995

[51] Int. Cl.[6] .................. A61M 1/00; A61L 2/18
[52] U.S. Cl. .................. 604/317; 604/319; 422/292
[58] Field of Search ............ 422/292, 302, 422/115, 116; 137/241, 240; 251/148; 604/317, 319, 320, 322, 324, 326

[56] References Cited

U.S. PATENT DOCUMENTS

| | | | |
|---|---|---|---|
| 2,936,757 | 5/1960 | Trace | 128/276 |
| 3,191,600 | 6/1965 | Everett | 128/276 |
| 3,929,133 | 12/1975 | Ragab | 128/277 |
| 4,054,998 | 10/1977 | Hesselgren | 32/33 |
| 4,090,502 | 5/1978 | Tajika | 128/2 A |
| 4,105,031 | 8/1978 | Kurtz et al. | 128/276 |
| 4,135,515 | 1/1979 | Muriot | 128/276 |
| 4,157,718 | 6/1979 | Baehr | 128/276 |
| 4,306,557 | 12/1981 | North | 128/276 |
| 4,333,480 | 6/1982 | Villari et al. | 128/767 |
| 4,464,258 | 8/1984 | Wong et al. | 210/205 |
| 4,493,695 | 1/1985 | Cook | 604/27 |
| 4,505,703 | 3/1985 | Gale et al. | 604/317 |
| 4,540,413 | 9/1985 | Russo | 604/320 |
| 4,626,248 | 12/1986 | Scheller | 604/319 |
| 4,627,833 | 12/1986 | Cook | 604/34 |
| 4,631,050 | 12/1986 | Reed et al. | 604/4 |
| 4,642,093 | 2/1987 | Härle | 604/54 |
| 4,770,787 | 9/1988 | Heath et al. | 210/646 |
| 4,781,707 | 11/1988 | Boehringer et al. | 604/317 |
| 4,808,159 | 2/1989 | Wilson | 604/4 |
| 4,855,064 | 8/1989 | Schlein | 210/764 |
| 4,857,063 | 8/1989 | Glenn | 604/317 |
| 4,863,446 | 9/1989 | Parker | 604/317 |
| 4,867,738 | 9/1989 | Mintz | 604/4 |
| 4,957,491 | 9/1990 | Parker | 605/317 |
| 4,986,839 | 1/1991 | Wertz et al. | 55/274 |
| 5,017,135 | 5/1991 | Meyer | 433/92 |
| 5,044,953 | 9/1991 | Sullivan | 433/92 |
| 5,045,077 | 9/1991 | Blake, III | 604/321 |
| 5,047,072 | 9/1991 | Wertz et al. | 55/1 |
| 5,053,025 | 10/1991 | Knippscheer | 604/317 |
| 5,078,677 | 1/1992 | Gentelia et al. | 604/4 |
| 5,154,712 | 10/1992 | Herweck et al. | 604/321 |
| 5,156,823 | 10/1992 | Hori et al. | 422/292 |
| 5,185,007 | 2/1993 | Middaugh et al. | 604/320 |
| 5,225,158 | 7/1993 | Tayebi et al. | 422/4 |
| 5,238,582 | 8/1993 | Hori et al. | 210/749 |
| 5,242,434 | 9/1993 | Terry | 604/317 |
| 5,277,869 | 1/1994 | Glazer et al. | 422/26 |
| 5,279,600 | 1/1994 | Hogan | 604/317 |
| 5,279,602 | 1/1994 | Middaugh et al. | 604/320 |
| 5,284,621 | 2/1994 | Kaufman | 422/32 |

Primary Examiner—John G. Weiss
Assistant Examiner—David J. Cho
Attorney, Agent, or Firm—Fay, Sharpe, Beall, Fagan, Minnich & McKee

[57] ABSTRACT

A collection vessel (20) is connected with inlet fitting assemblies (12, 14) for receiving waste fluids. The collection vessel is connected by a valve (74) with a drain (70) for selectively draining collected fluids. A fluid inlet (84) that is connected with an exterior water source supplies water through interconnecting tubing to rinse waste residue from the collection vessel. The water flows through a housing member (200) that surrounds a tubular member (214) of the inlet assembly. The housing member is spaced by spacers (216) from the bottom surface (220) of a well (210) surrounding the tubular member such that trapped water is drained through a drain outlet (222). Powdered reagent (170a, 170b) is received in a cup (26) that is carried by a drawer (160) to a position above a fluid mixing reservoir (124). A mechanical actuator (122) lifts a mechanical assembly (124) which defines the reservoir, forcing a cutting blade (180) to pierce and cut open the cup. A pump (128) recirculates the water through the reservoir (124) to make a disinfectant fluid concentrate which is supplied to a venturi (120) to be selectively entrained in the rinse water.

24 Claims, 4 Drawing Sheets

MEDICAL AND BIOLOGICAL FLUID COLLECTION AND DISPOSAL SYSTEM

BACKGROUND OF THE INVENTION

The present invention relates to the art of handling biological fluids. It finds particular application in conjunction with the collection, treatment, and disposal of fluid wastes in operating rooms, patient care rooms, emergency care units, and other medical facilities and will be described with particular reference thereto.

Heretofore, various techniques have been used for collecting waste body fluids in conjunction with medical procedures. The collection vessels varied from a simple plastic bag to automated, electrically controlled processing equipment.

The receiving receptacle often varied with the nature and volume of the fluids to be collected. Typical fluids have included blood, urine, mucous, and other body discharges. During some surgical procedures, such as joint surgery, a saline solution or other rinse and lubricating fluid was selectively introduced into the surgical site. The fluid was drawn off from time to time, removing with it surgical scraps, any blood, and other body fluids that may have entered into the surgical site.

Simple bags and pouches could be hung from the surgical table or placed at other convenient locations within the room in which the medical procedure was performed. Flexible tubing typically interconnected the bag with the region of the patient from which the fluid wastes were collected. Such bags or pouches had several drawbacks. First, safe disposal of the fluids was difficult. Such bags or pouches were typically emptied manually, creating the opportunity for direct human contact with potentially infected wastes. Second, difficulties could arise if the volume of drained fluid exceeded the capacity of the bag. Not only would the fluid not drain, but fluid in the bag and the connecting line would be under a positive pressure attributable to the fluid held in the line and resiliency of the bag or pouch. Disconnecting the lines, handling of the pouch, and the like could cause discarded fluids to be reintroduced into the patient or to spurt onto medical personnel, the wound site, or the like.

More elaborate electronically controlled fluid waste removal systems have been utilized, particularly where the fluid waste is removed under suction. Although electronically controlled and of larger capacity, the systems still suffered similar problems. Many required direct manual interaction with medical personnel in order to empty the wastes from the collection reservoir. Others lacked adequate safety features to assure that fluid in the flexible lines would not spurt or be forced back into the patient when the reservoirs become full or during disconnection of the lines. Typically, electronically controlled devices would be dedicated suction or gravity feed devices. In medical procedures in which both gravity and suction drain devices were required, two units would be needed.

Simple collection bags were often discarded as hazardous or potentially hazardous waste. The more complex systems required cleaning and maintenance. Typically, cleaning and maintenance required sufficient human interaction that the human operator was liable to come in contact with a contaminated and potentially infectious surface.

The present invention contemplates a new and improved biological fluid collection, handling, and disposal system which overcomes the above-referenced disadvantages and others.

SUMMARY OF THE INVENTION

In accordance with one aspect of the present invention, an apparatus is provided for handling biological and medical fluid wastes. At least one inlet fitting is interconnected with a flexible tube which is connected to a source of the fluid waste. A collection vessel is connected with the inlet fitting such that the received fluid waste flows into the collection vessel. A drain line is connected with the collection vessel for selectively draining the collection vessel. A rinse liquid inlet receives a source of rinse liquid. The rinse liquid inlet is interconnected by interconnecting tubing with the collection vessel for selectively rinsing waste fluid residue therefrom. A disinfectant liquid source selectively supplies a concentrated disinfectant liquid. The disinfectant source includes a reservoir for receiving powdered reagents which intermix with the rinse liquid to form a liquid disinfectant concentrate. The reservoir is interconnected with the rinse fluid inlet for receiving the rinse fluid therefrom, and is interconnected with the interconnecting tubing for entraining the disinfectant concentrate in the rinse liquid flowing therethrough.

In accordance with one aspect of the present invention, an apparatus is provided for handling biological and medical fluid wastes. At least one inlet fitting is interconnected with a flexible tube which is connected to a source of the fluid waste. A collection vessel is connected with the inlet fitting such that the received fluid waste flows into the collection vessel. A drain line is connected with the collection vessel for selectively draining the collection vessel. A rinse liquid inlet receives a source of rinse liquid. The rinse liquid inlet is interconnected by interconnecting tubing with the collection vessel for selectively rinsing waste fluid residue therefrom. A disinfectant source selectively supplies a concentrated disinfectant to the rinse liquid flowing through the interconnecting tubing. An over-fitting is interconnected with the interconnecting tubing for receiving the rinse liquid and the rinse liquid with entrained disinfectant. The over-fitting is selectively interconnectable with the inlet fitting for disinfecting the inlet fitting.

In accordance with a more limited aspect of the present invention, the inlet fitting includes a tubular fitting over which the flexible tube is frictionally received and an outer member which defines a well around the tubular fitting. The over-fitting includes a housing member which is received in the well in a fluid-tight relationship. The housing member has an enlarged inner area surrounding and spaced from the tubular fitting such that the rinse liquid flows freely around all surfaces of the tubular fitting.

In accordance with another aspect of the present invention, a planar cutting blade is provided for opening reagent packages. A pair of converging cutting edges are mounted at an angle to vertical for centering a received package and cutting a peripheral wall of the package upon further receipt. A plurality of points are disposed between the converging cutting edges for piercing a bottom wall of the package. Non-symmetric, sloping, cutting edges extend between the points and converging edges such that the received package is punctured, sliced, and ripped to assure opening of the package, even when the cutting edges become dulled.

In accordance with another aspect of the present invention, a self-disinfecting fitting assembly is provided. An inlet fitting includes a tubular member which frictionally receives tubing along its outer surface. The tubing member has an internal passage for receiving fluids from the tubing. An outer peripheral wall surrounds the tubular member and a base wall interconnects the peripheral wall and tubular member to define a well. A drain outlet extends from a region adjacent an intersection of the peripheral and base walls. A covering member includes a housing member having a peripheral edge which frictionally engages the inlet fitting peripheral wall in a fluid-tight seal. A plurality of projections hold the housing member offset from the inlet fitting base wall and define a fluid passage in fluid communication with the drain outlet. The housing member defines an internal chamber which surrounds the tubular member in a spaced relationship. A fluid inlet into the housing member internal chamber receives a disinfectant fluid.

In accordance with another aspect of the present invention, a method of handling medical and biological fluid waste is provided. The waste fluid is received from fluid lines connected with a source of the waste fluids and flows through an inlet fitting assembly and is collected in a collection vessel that is connected with the inlet assembly by interconnecting tubing. After collecting the fluid waste, the waste fluid is discharged through a drain outlet. Rinse water passes through the inlet assembly, the interconnecting tubing, and the collection vessel to rinse waste fluid residue. A powdered reagent is dissolved in the rinse water to form a disinfectant. The disinfectant is entrained in the rinse water flowing through the interconnecting tubing to form a disinfectant liquid. The inlet assembly, the interconnecting tubing, and the collection vessel are disinfected with the disinfecting fluid. The drain outlet is closed and a preselected volume of the disinfecting liquid is collected in the collection vessel.

One advantage of the present invention is that it is fully automatic. The potential for direct contact between a human patient or operator and the collected fluids is minimized.

Another advantage of the present invention is that it ensures the disinfection is conducted with a disinfectant solution of a predetermined concentration.

Another advantage of the present invention is that it minimizes the potential for fluid in flexible feed lines from spurting onto the patient, attendant, or wound site.

Another advantage of the present invention resides in the automatic decontamination of the apparatus which again minimizes the opportunity for human contact with disposed fluids.

Another advantage of the present invention resides in improved safety and warning features which inhibit misuse of the equipment.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
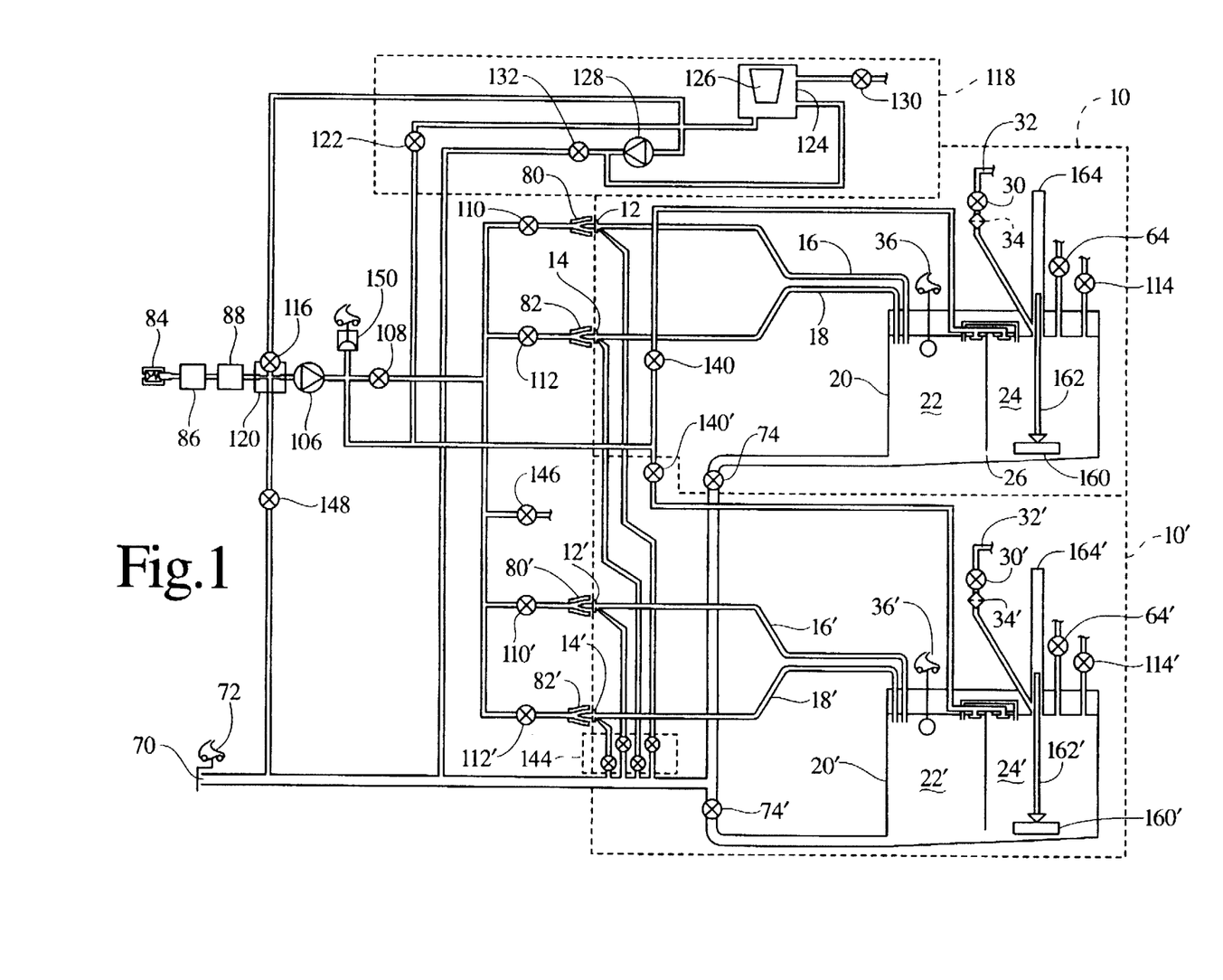
FIG. 1 is a diagrammatic illustration of a biological and medical fluid waste collection, handling, and discharge system in accordance with the present invention.

A common housing holds a first fluid waste receiving assembly 10 and a second fluid waste receiving assembly 10'. Fluid waste receiving assemblies 10 and 10' are significantly analogous that a detailed description will be made to the parts of assembly 10 and the description will be understood as describing the assembly 10' as well. Like parts in assembly 10' are denoted with the same reference numeral as in assembly 10 but followed by a prime (').

A pair of inlet fittings 12, 14 are rigidly mounted to a housing and configured to be received frictionally in flexible tubing which is connected with the patient or other source of fluid waste. The fittings are connected through inlet tubes 16, 18 with a fluid receiving vessel 20. More specifically, the fluid receiving vessel 20 has multiple chambers including a first chamber 22 and a second chamber 24 which are interconnected by a fluid level equalization path 26 adjacent a lowermost end of each. A pressure equalization passage 28 allows the fluid level in the first and second chambers to equalize. The inlet tubes 16, 18 have discharge ends disposed in an uppermost region of the first chamber 22. The fluid discharged from the inlet tubes into the first chamber 22 tends to be turbulent and may have froth or foam on its upper surface. The fluid connection passage 26 allows the least turbulent portion of the fluid at the bottom of the first chamber 22 to flow into the second chamber 24.

When fluid is being received, a valve 30 interconnects a line 32 through a filter 34 with the upper region of the second chamber 24. Line 32 is connected to a vacuum, such as the in-wall vacuum system found in most hospitals, if the fluid wastes are to be drawn in under a vacuum or connects with atmosphere if the fluid wastes are to be drained by gravity flow. As the fluid level within the chambers rises, a level sensor such as a float switch 36 senses the level of the fluid in the vessel 20. The level sensor 36 sends signals to an electronic control circuitry 40 indicative of the level of fluids in the vessel 20. Before the level of the fluid reaches the lowermost surface of the inlet tube 16, 18, the collection of fluid wastes is terminated.

Figure 2:
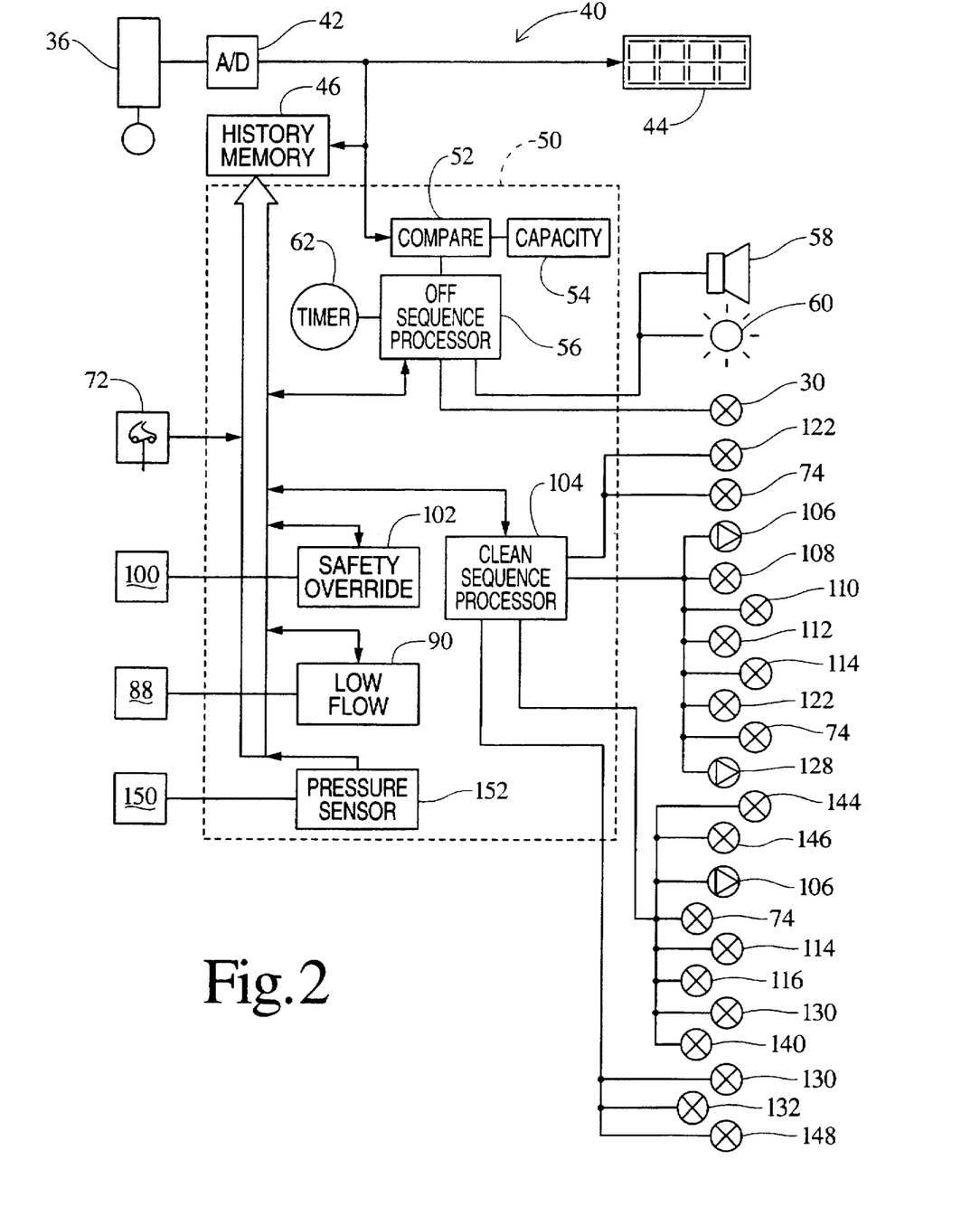
FIG. 2 is a diagrammatic illustration of an electronic control circuit in accordance with the present invention for the system of FIG. 1.

With continuing reference to FIG. 1 and further reference to FIG. 2, an electronic control 40, among other operations, terminates venting/suction when the vessel 20 becomes filled. More specifically, the output of the level sensor 36 is conveyed to an analog-to-digital converter 42 which digitizes the level signal. A digital display 44 provides the operator with a digital display of capacity remaining. Alternately, the digital display 44 can provide an indication of the volume of fluid collected. The received fluid and level information is stored in a history memory 46.

A microprocessor controller 50 includes a comparator 52 which compares the digital fluid level signal with a capacity from a capacity memory 54. When the full capacity is reached, the comparator starts an off or termination sequence processor 56. Initially upon reaching capacity, the off sequence processor 56 actuates an audio alarm 58 and a visual alarm 60. A predetermined time later, e.g., 30 seconds, as determined by a timer 62, or a predetermined fluid level increase later as determined from the digital level signal from the level sensor 36, the off sequence processor closes valve 30. If the system is connected with a vacuum source, this terminates the draw of the vacuum source. If connected to atmosphere for gravity drain, this closes the atmospheric vent to create backpressure terminating the ingress of fluid wastes. The off sequence processor communicates the level, time, and other termination sequence information to the history memory 46. A manually operated valve 64 is selectively operated by the attendant after the inlet ends of the flexible tubing have been disconnected from the source of the fluid waste. Opening valve 64 again vents the vessel 20 to atmosphere, allowing any residual pressure in the lines and the inlet tubes 16, 18 to be safely relieved to atmosphere. The inlet fittings 22 and 12, are physically positioned at a higher elevation than the top of the vessel 20 such that gravity causes any remaining fluids therein to flow into the vessel 20.

When the flexible waste tubes are disconnected from the collection system 10, they may be reconnected immediately to collection system 10' for the collection of further fluids, unless system 10' is already connected to other sources of fluid waste or is filled to capacity.

In the preferred portable embodiment, the collection systems 10, 10' are housed in a common wheeled housing. After the vessels are filled, the housing is wheeled to a drain into which the fluids in the vessels 20 and 20' are drained. For most biological fluids, the drain can be a standard sanitary or sewer drain. The waste biological fluids present a biological load to the sewage treatment station which is analogous to the load traditionally sent into sewage treatment stations. Once an outlet is positioned adjacent or in the receiving drain, an attendant connects a drain hose outlet 70 to a drain hose which direct effluent to a drain. A drain hose sensor switch 72 checks the presence of the drain hose to assure that a drain valve 74 will not be opened in its absence. The attendant further connects self-disinfecting over-fittings 80, 82 with the inlet fittings 12, 14. The fittings 80, 82 are connected to flexible fluid supply tubing lengths which extend out of the housing. In the portable unit, a water inlet fitting 84 is interconnected with a source of water. In the built-in embodiment, the system is connected directly with the plumbing system of the building. During a clean cycle, a pressure regulator 86 limits the pressure of the incoming water. A flow monitor 88 monitors the flow rate of the received water. The flow monitor 88 produces a digital output signal indicative of the flow rate, which output signal is conveyed to the history memory 46 and to a low flow rate warning circuit 90. The flow rate warning circuit compares the flow rate with an appropriate flow rate for the current cycle as supplied by the history memory 46. When an insufficient fluid flow rate is provided, the flow rate sensor triggers an alarm 92 to alert the attendant that there is insufficient water flow for proper operation.

In a stationary embodiment, the housing is mounted to a wall in the medical facility and the outlet is permanently connected with sanitary plumbing of the building. In the stationary embodiment, a drain outlet 70 and a drain hose sensor switch 72 are not strictly necessary for operation but are preferably still retained for such times as when maintenance dictates removal of the entire assembly from the wall mounting. In the stationary embodiment, the off sequence processor 56 automatically opens the drain valve 74 when the level sensor 36 senses that the fluid level in the vessel 20 is at or is approaching capacity.

The operator depresses a button 100 to initiate draining of the vessel 20 and begin the clean cycle. When this occurs, a safety override circuit 102 queries the history memory 46 to determine whether the system is in an appropriate state to be drained. If the history memory 46 is in the appropriate state to be drained, then the safety override allows the drain valve 74 to be opened. For safety, the drain hose presence switch 72 detects that a drain hose has been connected to the unit. That information is communicated to the history memory 46. If the drain hose is not connected, the safety override 102 prevents the valve 74 from opening. Analogously, if the drain hose is connected, the safety override 102 allows the drain valve 74 to open and vessel 20 drains.

Upon completion of draining the vessel 20, and if everything is in the appropriate state for the cleaning cycle, a cleaning sequence processor 104 actuates a pump 106, opens a fluid inlet valve 108, and opens fluid inlet valves 110, 112 concurrently or sequentially. Depending on water pressure and flow rates, fittings 12 and 14 may be cleaned concurrently or sequentially. Analogously, vessels 20 and 20' may be cleaned either concurrently or sequentially. While the water is flowing through the inlet fittings 12 and 14, the cleaning sequence processor maintains the drain valve 74 in an open state so that the rinse water can drain and opens a valve 114 or the valve 30 to vent the vessel to atmosphere.

In order to disinfect the inlets 12, 14, the tanks 20, and other portions of the system, a disinfectant supply valve 116 is opened. The disinfectant supply valve supplies a disinfectant concentrate from a disinfectant concentrate supply 118 to a venturi block 120. The venturi, which is preferably integral with the supply valve 116, introduces a metered concentration of the disinfectant into water flowing into the system.

The disinfectant supply system 118 includes an inlet valve 122 is opened until the disinfectant supply system is filled to a preselected level. A reservoir 124 receives a unit dose of a powdered reagent, preferably from a single use cup or cartridge 126. As explained below in greater detail in conjunction with FIG. 3, the cartridge 126 is opened, releasing the powdered material. A pump 128 recirculates the received water through the chamber 124 until the powdered reagents are dissolved and react to form a disinfectant concentrate. When the disinfectant supply valve 116 is opened, a vent valve 130 is also opened to enable the venturi 120 to draw the disinfectant concentrate into the water supply stream. After the disinfectant supply valve 116 is closed at the end of the cleaning cycle, a disinfectant drain valve 132 is opened to drain any leftover disinfectant concentrate to the drain outlet 70. In this manner, a unit dose of new disinfectant is mixed for each disinfectant cycle.

After the contents of the tank 20 have been drained through the outlet valve 74 and the inlet fittings 12, 14 have been flushed, valves 108, 110, and 112 are closed as valve 140 is opened, such that the interior of the tank sections 22, 24 are flushed out by water through spray heads 142. After the fittings and tanks have been flushed, valve 140 is closed and valves 108, 110, 112, and 116 are opened to supply disinfectant through the inlet fittings 12, 14. After a preselected duration, the valves 108, 110, and 112 are again closed and valve 140 is opened such that the disinfectant material is sprayed into the tank 20, disinfecting the walls of chambers 22, 24. An array of drain valves 144 and vent valve 146 are also opened to allow any disinfectant solution trapped in the fittings 12, 14 to drain. After a preselected duration, the drain valve 74 is closed, allowing disinfectant solution to pool in the bottom of the tank 20. After a further preselected duration keyed to place a preselected volume of disinfectant within the tank 20, the pump 106 is stopped and valves 116, 140 and 144 are closed. Thereafter, the drain valve 132 and a drain valve 148 are opened to allow extra disinfectant and fluid in the system to be drained to the drain outlet 70.

A pressure switch 150 is connected adjacent an output end of the pump 106 and with the memory history 46. An over/under pressure sensor 152 compares the pressure from the pressure sensor 150 with acceptable operating pressures for the pump. In an over/under pressure situation, the pressure indicator switch through the memory history and the safety overrides terminates operation of the pump and alerts the attendant of a malfunction.

In addition to the digital readout 44, a mechanical indicator of fluid level in the vessel 20 is provided. More specifically, a float 160 is interconnected with a float rod 162. The float rod 162 extends through an at least partially transparent sealed tube 164 at the top of the vessel 20. The level of the float rod 162 in the tube 164 is indicative of the level to which the vessel 20 is filled.

Figure 3:
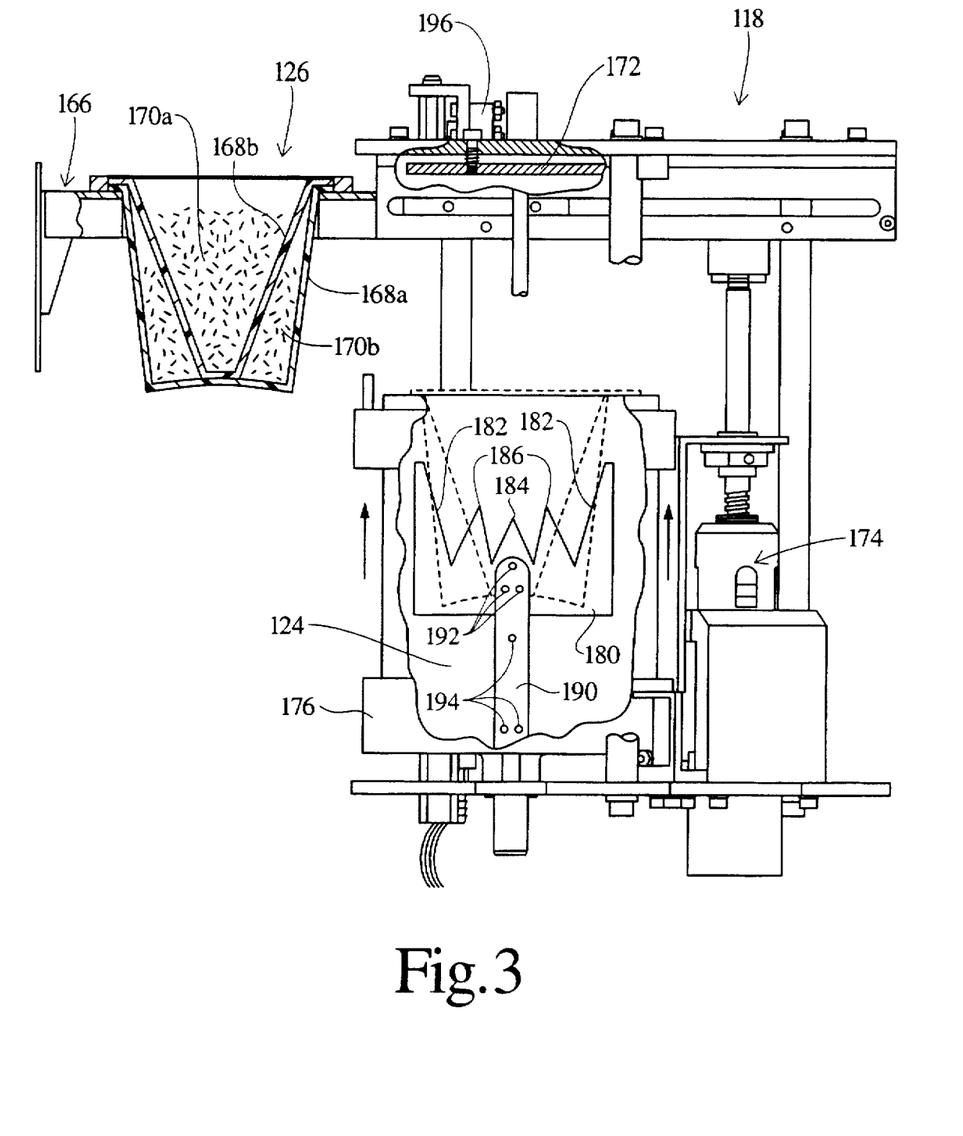
FIG. 3 is a diagrammatic illustration of an assembly of the system of FIG. 1 for opening disinfectant cartridges.

With reference to FIG. 3, the disinfectant supply 118 includes a slide drawer or tray 166 that defines a cup or cartridge receiving aperture therein for receiving the cup or cartridge 26. In the preferred embodiment, the cassette 126 is a two compartment cup constructed of a thin polyethylene or other plastic material. An outer cup 168a receives a more tapered inner cup 168b therein. The inner and outer cups meet at the base in a truss-like configuration to inhibit collapsing of the cup. The cup defines two chambers, an outer chamber 170b which contains one component in powdered form and an inner chamber 170a which contains another component in powdered form. Preferably, the powdered components are reagents which interact in the presence of water to form a strong oxidant, such as peracetic acid, lithium hypochlorite, or other materials having antimicrobial activity.

The drawer with the received cup is slid inward with a spring-biased plate 172, urging the cup firmly downward against the drawer. A mechanical actuator assembly 174 selectively raises a mechanical assembly 176 which defines the mixing chamber 124 therein. After the cup and drawer are slid in, the mechanical actuator 174 raises the mechanical assembly, 176 until it presses firmly around the cup, defining a closed chamber.

A cup cutting blade 180 is disposed in the chamber. The cutting blade has sharpened side edges 182 which initially engage peripheral edges of the cup, centering it and holding it in a centered configuration as the assembly 176 continues to raise. With further lifting of the assembly, the centering edges 182 cut into sides of the cup as a center peak 184 and intermediate peaks 18 pierce the bottom of the cup. With continued rising of the assembly 176, non-symmetric taper angles on the cutting edges of peaks 184 and 186 slice and rip open the inner and outer cups.

The blade is supported on a tubular member 190 in fluid communication with the pump 128. The tubular member 190 includes a plurality of jets 192 which are aimed up into the inner and outer cups to flush all powdered reagents from the cup. Additional jets 194 assure that all powdered reagents which fall from the cup are flushed into the recirculating liquid and dissolved. A limit switch 196 senses the resistance as the blade engages the cup. If the cup is full, there is sufficient resistance to lift the plate 170 and engage the limit switch. If the cup was previously used, there is too little resistance to lift the plate. The failure to sense the resistance of cutting into a full cup is transmitted to the processor 50 which causes an appropriate alarm to be generated.

Figure 4:
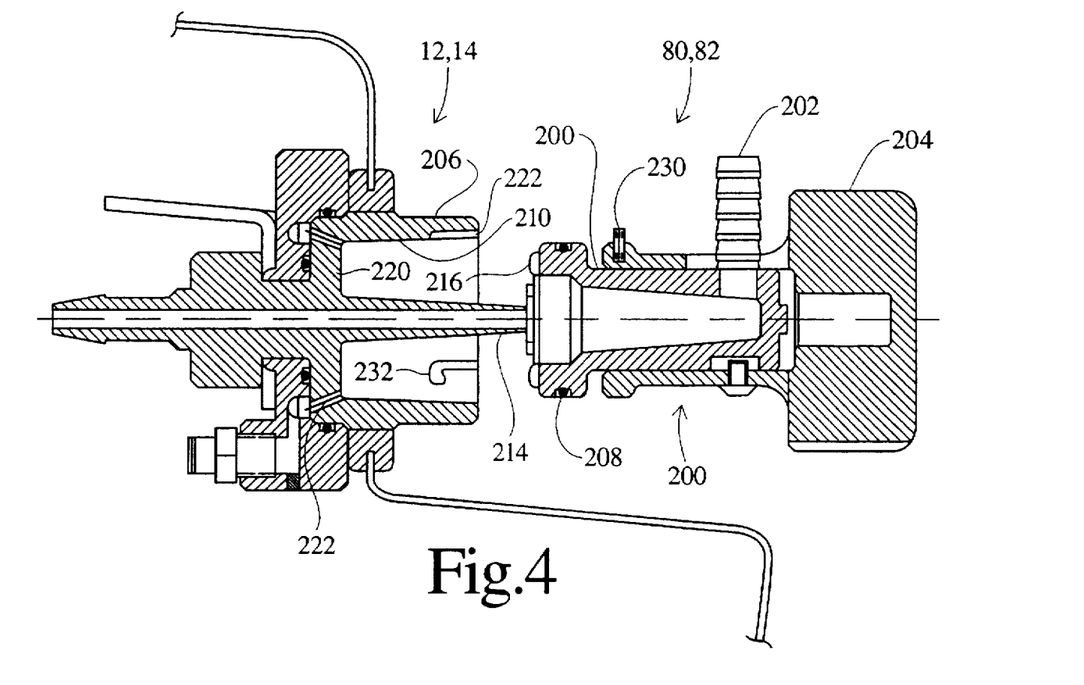
FIG. 4 is a detailed sectional view of a self-sterilizing fluid coupling assembly in accordance with the present invention in a detached configuration; and, FIG. 5 is a detailed sectional view of the self-sterilizing fluid coupling of FIG. 4 in a connected configuration.
Figure 5:
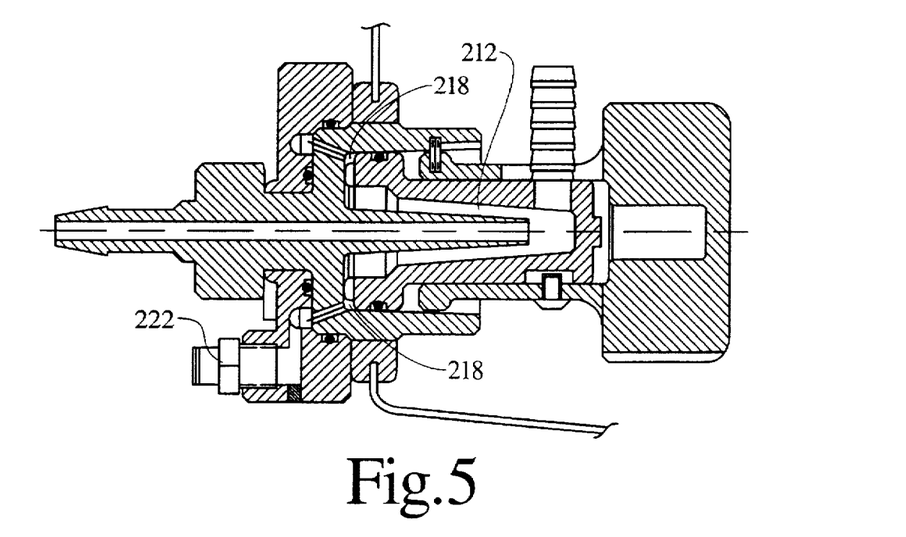

With reference to FIGS. 4 and 5, the over-fittings 80, 82 each include a housing member 200 which is connected by a fitting 202 with the valve 110, 112. The housing member is connected to a handle portion 204 to facilitate manual insertion into a socket member 206 of the fitting 12, 14. As the removable portion is inserted, sealing surface 208 engages a peripheral wall 210 of an inner well of the socket member 206 in a sealing relationship therewith. The housing member 200 defines a spaced chamber 212 around a tubular fitting 214 to which flexible tubing leading to a site to be drained is selectively connected. The housing member 200 includes a plurality of spaced projections 216 adjacent one end. The projections are spaced from an outer periphery to define an annular passage 218 around an inner wall 220 of the socket 206 in fluid communication with a drain outlet 222.

After the system has been used to receive medical wastes, the tubing leading to the source of medical waste is removed from the tubular fitting 214. The housing member 200 is inserted into the socket 206 until pins 230 are received and lock in grooves 232 in a bayonet type interconnection. Initially water is received through the inlet 202 into the chamber 212 flushing the exterior of the tubular fitting 214 and its interior passage. Then, water with disinfectant is passed through the same path, disinfecting all exterior and interior surfaces of the tubular fitting 214. After stopping the circulation of disinfectant, any disinfectant remaining in the chamber 212 drains through passage 218 and drain 222. Thereafter, an operator can remove the removable portion to gain access to the tubular fitting 214 assured that all operator accessible surfaces have been disinfected.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An apparatus for handling biological and medical fluid wastes, the apparatus comprising:
   at least one inlet fitting for interconnection with a flexible tube which is connected with a source of the fluid waste;
   a collection vessel connected with the inlet fitting such that received fluid waste flows into the collection vessel;
   a drain line connected with the collection vessel for selectively draining the collection vessel;
   a rinse liquid inlet for receiving a source of rinse liquid, the rinse liquid inlet being interconnected by interconnecting tubing with the collection vessel for selectively rinsing waste fluid residue therefrom;
   a disinfectant liquid source for selectively supplying a concentrated disinfectant liquid, the disinfectant source including;
      a reservoir for receiving single-use powered reagent canisters including powdered reagents which intermix with the rinse liquid to form the liquid disinfectant concentrate, the reservoir being interconnected with the rinse fluid inlet for receiving the rinse liquid therefrom and being interconnected with the interconnecting tubing for entraining the disinfectant concentrate in the rinse liquid flowing therethrough;
      a cutter disposed in the reservoir for opening powdered reagent canisters received therein; and,
      a mechanical actuator for moving the cutter to engage the canisters such that the cup is forced open to release the powered reagents.

2. The apparatus as set forth in claim 1 wherein the powdered reagent canister includes a cup having peripheral side walls and a base wall and wherein the cutter has a pair of oppositely disposed sloping first cutting edges which engage the cup peripheral side walls as the cup is received centering the cup and upon further receipt slicing into the peripheral side walls and at least one piercing point having sloping side cutting edges dependent therefrom for piercing the base wall of the cup and slicing the cup open.

3. The apparatus as set forth in claim 2 further including additional piercing points and sloping, non-symmetric cutting edges.

4. The apparatus as set forth in claim 2 further including a platen which is resiliently biased against an upper surface of the cup and a limit switch which is tripped by force generated as the cutter is pressed against a full cup, but which is not tripped when the cutter engages a cup which has already been cut open.

5. The apparatus as set forth in claim 1 further including a tubular member supporting the cutter, the tubular member being interconnected with a pump which pumps rinse liquid into the tubular member, the tubular member having a plurality of apertures for rinsing powdered reagents from an interior of the canister and from an interior of the reservoir, the pump being interconnected with the reservoir for recirculating rinse liquid therethrough to assure that the powdered reagents become fully dissolved in the rinse liquid.

6. The apparatus as set forth in claim 1 wherein the cutting blade includes:
   a pair of converging edges mounted at an angle to vertical for centering the received reagent canister and cutting a peripheral wall of the canister upon further receipt;
   a plurality of points for piercing a bottom wall of the canister;
   sloping cutting edges extending between the points and the converging cutting edges, such that the received package is sliced, punctured, and ripped to assure opening of the package, even when the cutting edges become dulled.

7. The apparatus as set forth in claim 1 wherein the rinse liquid inlet and the concentrated disinfectant liquid source are interconnected with a venturi assembly such that the rinse liquid passing through the venturi assembly draws the concentrated disinfectant liquid into the flow.

8. The apparatus as set forth in claim 7 wherein the venturi assembly is a unitary element which is integrally connected with a valve which selectively controls disinfectant liquid concentrate flows to the venturi assembly.

9. The apparatus as set forth in claim 1 further including an over-fitting interconnected with the interconnecting tubing for receiving the rinse liquid and the rinse liquid with entrained disinfectant therefrom, the over-fitting being selectively interconnectable with the inlet fitting for disinfecting the inlet fitting.

10. An apparatus for handling biological and medical fluid wastes, the apparatus comprising:
    at least one inlet fitting for interconnection with a flexible tube which is connected with a source of the fluid waste;
    a collection vessel connected with the inlet fitting such that received fluid waste flows into the collection vessel;
    a drain line connected with the collection vessel for selectively draining the collection vessel;
    a rinse liquid inlet for receiving a source of rinse liquid, the rinse liquid inlet being interconnected by interconnecting tubing with the collection vessel for selectively rinsing waste fluid residue therefrom;
    a slidable drawer having an aperture within which a powdered reagent cup is received, the drawer being slidable between a cup receiving position and a second position;
    a mechanical actuator for selectively engaging the cup when the drawer is in the second position such that the cup is forced open to release powdered reagents therefrom;
    a reservoir for receiving the powdered reagents released from the cup, the reservoir being interconnected with the rinse liquid inlet for receiving the rinse liquid and intermixing the rinse liquid with the powdered reagents to form a liquid disinfectant concentrate, the reservoir being interconnected with the interconnecting tubing for supplying the disinfectant concentrate to the collection vessel.

11. An apparatus for handling biological and medical fluid wastes, the apparatus comprising:
    at least one inlet fitting for interconnection with a flexible tube which is connected with a source of the fluid waste, said inlet fitting including:
       a tubular fitting over which the flexible tube is frictionally received, and
       a socket member defining a well around the tubular fitting;
    a collection vessel connected with the inlet fitting such that received fluid waste flow into the collection vessel;
    a drain line connected with the collection vessel for selectively draining the collection vessel;
    a rinse liquid inlet for receiving a source of rinse liquid, the rinse liquid inlet being connected with interconnecting tubing;
    a disinfectant concentrate source for selectively supplying a concentrated disinfectant liquid, the disinfectant source being selectively connected to the interconnecting tubing to receive rinse liquid therefrom and supplying a disinfectant solution thereto;
    an over-fitting interconnected with the interconnecting tubing for receiving the rinse liquid and the rinse liquid and the disinfectant solution therefrom, the over-fitting being selectively interconnectable with the inlet fitting for cleaning and disinfecting exterior and interior surface of the inlet fitting, said over-fitting including:
       a housing member which is received in the well in a fluid tight relationship, the housing member having an enlarge inner area surrounding the tubular fitting to provide free fluid flow all around the tubular fitting.

12. An apparatus for handling biological and medical fluid wastes, said apparatus comprising:
    at least one inlet fitting for interconnection with a flexible tube which is connected with a source of the fluid waste, said inlet fitting including:
       a tubular fitting over which the flexible tube is frictionally received, and
       a socket member defining a well around the tubular fitting;
    a collection vessel connected with the inlet fitting such that received fluid waste flows into the collection vessel;
    a drain line connected with the collection vessel for selectively draining the collection vessel;
    a rinse liquid inlet for receiving a source of rinse liquid;
    an over-fitting interconnected with the rinse liquid inlet and a disinfectant liquid source for receiving the rinse liquid and disinfectant liquid therefrom, the over-fitting being selectively interconnectable with the inlet fitting for cleaning and disinfecting the inlet fitting, said over-fitting including a housing member which is received in the well in a fluid tight relationship with a side wall of the well, the housing member having:
an enlarged inner area surrounding the tubular fitting to provide free fluid flow all around the tubular fitting, and
a plurality of spacers adjacent an innermost end thereof for holding the housing member displaced from an inner wall of the well and defining a drain passage therearound, the drain passage being interconnected through the well with the drain line.

13. The apparatus as set forth in claim 12 wherein the over-fitting further includes a handle member within which the housing member is slidably received, the handle member having pins for interconnection with pin receiving grooves in the well that define a bayonet type coupling.

14. An apparatus for handling biological and medical fluid wastes, the apparatus comprising:
at least one inlet fitting including:
a tubular member for frictionally receiving tubing along an outer surface thereof, the tubular member having an internal passage for receiving flexible tube which is connected with a source fluid waste from the tubing;
an outer peripheral wall surrounding and spaced from the tubular member;
a base wall interconnecting the peripheral wall and the tubular member to define a well around the tubular member;
a drain outlet extending from a region adjacent an intersection of the peripheral and base walls;
a collection vessel connected with the inlet fitting such that received fluid waste flows into the collection vessel;
a drain line connected with the collection vessel for selectively draining the collection vessel;
a rinse liquid inlet for receiving a source of rinse liquid, the rinse liquid inlet being interconnected by interconnecting tubing with the collection vessel for selectively rinsing waste fluid residue therefrom;
a disinfectant source for selectively supplying a concentrated disinfectant to the rinse liquid flowing through the interconnecting tubing; and,
an over-fitting interconnected with the interconnecting tubing for receiving the rinse liquid and a rinse liquid disinfectant solution therefrom, the over-fitting being selectively interconnectable with the inlet fitting for cleaning and disinfecting the inlet fitting, said over fitting including:
a housing member having a peripheral edge which engages the inlet fitting peripheral wall in a fluid tight seal;
a plurality of projections for holding the housing member offset from the inlet fitting base wall and defining a fluid passage in fluid communication with the drain outlet such that the housing member defines an internal chamber which surrounds the tubular member in a spaced relationship thereto; and
a fluid inlet into the housing member internal chamber for receiving a disinfectant and rinse liquid solution.

15. The apparatus as set forth in claim 14 wherein said over-fitting further includes a handle portion that facilitates manual holding thereof, and a locking mechanism for selectively locking the housing member to the inlet fitting.

16. An apparatus for handling biological and medical fluid wastes, the apparatus comprising:
at least one inlet fitting for interconnection with a flexible tube which is connected with a source of the fluid waste;

a collection vessel connected with the inlet fitting such that received fluid waste flows into the collection vessel;
a drain line connected with the collection vessel for selectively draining the collection vessel;
a rinse liquid inlet for receiving a source of rinse liquid, the rinse liquid inlet being interconnected by interconnecting tubing with the collection vessel for selectively rinsing waste fluid residue therefrom;
a disinfectant source for selectively supplying a concentrated disinfectant to the rinse liquid flowing through the interconnecting tubing, said disinfectant source including:
a powdered reagent canister receiving assembly including a drawer having a canister receiving aperture formed therein, said drawer movable between a canister receiving position providing access to said aperture and a second position;
a reservoir for receiving powdered reagents from a canister supported by said drawer which intermix with the rinse liquid to form the liquid disinfectant concentrate, the reservoir being interconnected with the rinse fluid inlet for receiving the rinse fluid therefrom and being interconnected with the interconnecting tubing for entraining the disinfectant concentrate and rinse liquid flowing therethrough;
a movable ram disposed in the reservoir for opening powdered reagent canisters to release the powdered reagents into the reservoir;
an over-fitting interconnected with the interconnecting tubing for receiving the rinse liquid and the rinse liquid with entrained disinfectant therefrom, the over-fitting being selectively interconnectable with the inlet fitting for disinfecting the inlet fitting.

17. The apparatus as set forth in claim 16 wherein the powered reagent canister has side walls and a base wall and wherein the cutter member has:
a pair of oppositely disposed converging cutting edge which engage the side walls as the canisters is received center the canister and upon further receipt slicing into side walls; and
at least one piercing point having sloping cutting edge dependent therefrom for piercing the bottom of the cup and slicing the cup open.

18. The apparatus as set forth in claim 17 further including a tubular member supporting the cutter, the tubular member having a plurality of apertures for rinsing powered reagent from the interior of the canister and from an interior of the reservior.

19. The apparatus as set forth in claim 16 wherein the inlet fitting includes a tubular fitting over which the flexible tube is frictionally received and an outer member defining a well around the tubular fitting and wherein the over-fitting includes a housing member which is received in the well in a fluid tight relationship, the housing member having an enlarged inner area surrounding and spaced from the tubular fitting such that the rinse liquid flows freely around all surfaces of the tubular fitting.

20. The apparatus as set forth in claim 19 wherein the housing members further includes a plurality of spacers adjacent an innermost end thereof for holding the housing member displaced from an inner wall of the well and defining a drain passage therearound, the drain passage being interconnected through the well with the drain line.

21. The apparatus as set forth in claim 16 further comprising a planar cutting blade for cutting open a powdered reagent canister, the cutting blade including:

a pair of converging cutting edges mounted at an angle to vertical for centering a received package and cutting a peripheral wall of the package upon further receipt;

a plurality of points disposed between the converging cutting edges for piercing a bottom wall of the package;

non-symmetric sloping cutting edges extending between the points and the converging cutting edges, such that the received package is sliced, punctured, and ripped to assure opening of the package, even when the cutting edges become dulled.

22. A method of handling medical and biological fluid waste, the method comprising:

receiving the waste fluid from fluid lines connected with a source of the waste fluids through an inlet fitting assembly and collecting the fluid waste in a collection vessel that is interconnected with the inlet assembly by interconnecting tubing;

after collecting the fluid waste, discharging the fluid waste through a drain outlet;

passing rinse water through the inlet assembly, the interconnecting tubing, and the collection vessel to rinse waste fluid residue;

loading a unit-dose powdered reagent containing canister into a rinse water receiving area;

accessing the canister and dissolving a powdered reagent in the rinse water to form a disinfectant and entraining the disinfectant in the rinse water flowing through the interconnecting tubing to form a disinfecting liquid;

disinfecting the inlet assembly, the interconnecting tubing, and the collection vessel with the disinfecting liquid;

closing the drain outlet and depositing a preselected volume of the disinfecting liquid in the collection vessel.

23. The method as set forth in claim 22 wherein the powdered reagent containing canister is placed into a mixing vessel, and wherein said canister is accessed by cutting open the canister as it is inserted into the mixing vessel, the method further including:

recirculating the rinse water through the mixing vessel to dissolve all of the powdered reagents from the canister into the water to form the disinfectant.

24. The method as set forth in claim 22 wherein the inlet fitting assembly includes a tubular member surrounded by a well having a drain outlet therethrough and a removable cover member which defines an internal chamber surrounding the tubular member, the tubular member being selectively connected with the fluid waste line, the method further including:

circulating the disinfecting liquid within the internal chamber surrounding the tubular member;

after stopping the flow of disinfecting liquid, draining residual disinfecting liquid from the well through the drain outlet.

* * * * *